United States Patent [19]

Ebata et al.

[11] Patent Number: 4,772,373
[45] Date of Patent: Sep. 20, 1988

[54] VERTICAL SLAB TYPE ELECTROPHORESIS APPARATUS

[75] Inventors: Nobuyoshi Ebata; Yumi Teramura; Miyoshi Hirata; Yoshio Sugimura, all of Tokyo, Japan

[73] Assignee: Daiichi Pure Chemicals Co., Ltd., Tokyo, Japan

[21] Appl. No.: 921,386

[22] Filed: Oct. 22, 1986

[30] Foreign Application Priority Data

Nov. 19, 1985 [JP] Japan .................... 60-268645

[51] Int. Cl.$^4$ ........................................ G01N 27/26
[52] U.S. Cl. ........................... 204/299 R; 204/182.8
[58] Field of Search ............. 204/299 R, 182.8, 182.9

[56] References Cited

U.S. PATENT DOCUMENTS

| | | | |
|---|---|---|---|
| 3,932,265 | 1/1976 | Hoefer | 204/299 R |
| 4,035,377 | 7/1977 | Detroy | 204/299 R |
| 4,142,960 | 3/1979 | Hahn et al. | 204/299 R |
| 4,339,327 | 4/1981 | Tyler | 204/299 R |
| 4,518,476 | 5/1985 | Delony et al. | 204/299 R |
| 4,574,040 | 3/1986 | Delony et al. | 204/299 R |
| 4,576,693 | 3/1986 | Kreisher et al. | 204/299 R |
| 4,707,235 | 11/1987 | Englert et al. | 204/182.8 |

FOREIGN PATENT DOCUMENTS

| | | |
|---|---|---|
| 0113700 | 7/1984 | European Pat. Off. |
| 1067310 | 5/1967 | United Kingdom |
| 2008151 | 5/1979 | United Kingdom |
| 2157443 | 10/1985 | United Kingdom |
| 2164584 | 3/1986 | United Kingdom |
| 8600708 | 1/1986 | World Int. Prop. O. |

Primary Examiner—John F. Niebling
Assistant Examiner—John S. Starsiak, Jr.
Attorney, Agent, or Firm—Oblon, Fisher, Spivak, McClelland & Maier

[57] ABSTRACT

A novel vertical slab type electrophoresis apparatus, characterized by the provision of a gel holding glass sheet couple detachably fitted in a pair of tapered fitting groove formed opposingly on and along the entire length of glass support column portions of a buffer solution chamber by means of wedge-like fixing bars having an outer shape corresponding to the internal wall shape of said fitting groove.

The electrophoresis apparatus precludes distortion of the gel which is gripped between the coupled glass sheets, permitting to obtain excellent migration images while preventing fracture of the glass sheets.

7 Claims, 9 Drawing Sheets

VERTICAL SLAB TYPE ELECTROPHORESIS APPARATUS

BACKGROUND OF THE INVENTION

1. Field of the Invention

This invention relates to a vertical slab type electrophoresis apparatus, and more particularly to a vertical slab type electrophoresis apparatus which is capable of fixedly holding a gel holding glass sheet couple with uniform force and in a facilitated manner.

2. Description of the Prior Art

Figure 10:
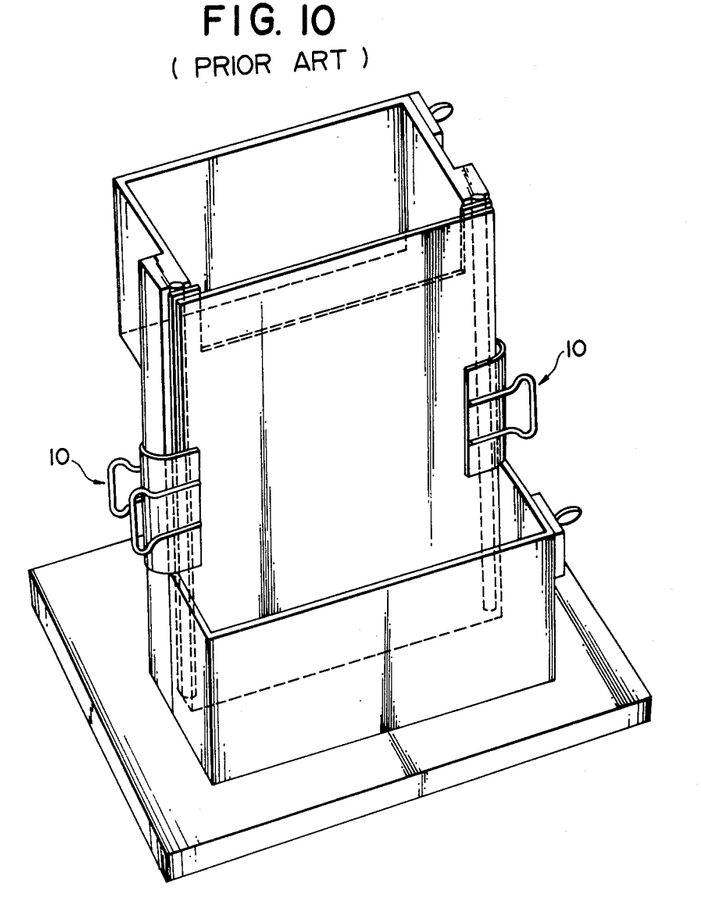
FIG. 10 (PRIOR ART) is a perspective view of a conventional electrophoresis apparatus.

The vertical slab gel electrophoresis system which is superior to the disk type electrophoresis system in operationability and resolution and which is capable of two-dimensional development is frequently used these days as a means suitable for separation and analysis of biological components such as proteins, nucleic acids and the like. The conventional apparatus employed for such electrophoresis processes usually have a gel holding glass sheet couple connected to a buffer liquid chamber by fixing the opposite sides of the glass sheets to support column portions by the use of clips 10 or screws or by fixing arbitrary points by the means of wedges (FIG. 10).

However, electrophoresis apparatus with such fixing means are found to be unsatisfactory because of the problems arising from uneven force of retention and fixation, e.g. distortion of gels, deterioration of migration images and fracture of glass sheets.

SUMMARY OF THE INVENTION

The present inventors have conducted an intensive study in search for a solution to the above-mentioned problems, and as a result found that the migration image can be improved to a marked degree by fixing the paired gel holding glass sheets with uniform force by the means of tapered fitting groove in combination with wedge-like fixing bars.

More particularly, in accordance with the present invention, there is provided a vertical slab type electrophoresis apparatus including a gel holding glass sheet couple, characterized in that the apparatus comprises: a pair of tapered fitting groove formed opposingly on and along the entire length of glass support column portions of a liquid buffer chamber for receiving the opposite sides of the couple of gel holding glass sheets; and wedge-like fixing bars having an outer shape corresponding to the inner wall shape of the glass fitting groove and engageable in the fitting groove to fix the glass sheets detachably therein.

DETAILED DESCRIPTION OF THE INVENTION AND PREFERRED EMBODIMENTS

Hereafter, the invention is described more particularly by way of preferred embodiments shown in the drawings.

Figure 8:
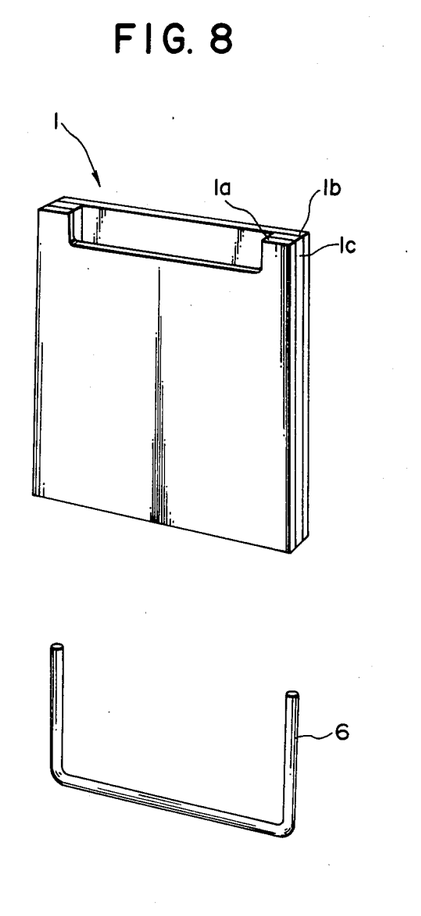
FIGS. 8 and 9 are perspective views showing in separated state the glass sheet couple and packing.
Figure 9:
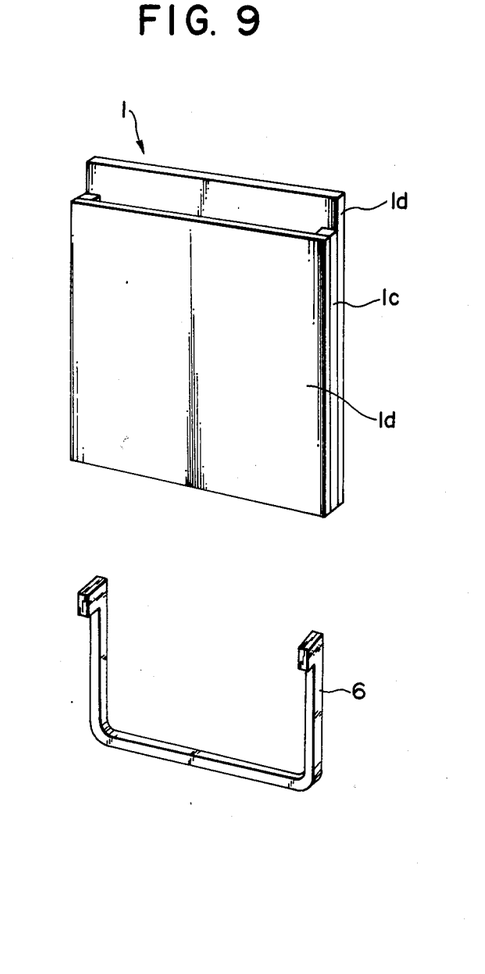

In the various figures, indicated at 1 is a gel holding glass sheet couple for grippingly holding a migration gel between two glass sheets. This gel holding glass couple may be constructed in an arbitrary form, for example, may be constituted by; a pair of glass sheets 1a and 1b which are bonded to each other through spacers 1c, one glass sheet 1a having an indented upper edge connecting the column portion 3 while the other glass sheet 1b is provided with a straight upper edge (FIG. 8); or a pair of straight-edged glass sheets 1d of different heights or lengths, which are bonded to each other through spacers 1c in such a manner that the upper edge of one glass sheet falls short of the other glass sheet (FIG. 9).

The reference numeral 2 denotes a chamber forming structure cooperating with the gel holding glass sheet couple to form a chamber of a buffer liquid trough which may be of the type having inner and outer chambers or of the type having upper and lower chambers.

Indicated at 3 are elongated glass support column portions which are formed in suitable positions depending upon the shape of the buffer liquid chamber.

Figure 4:
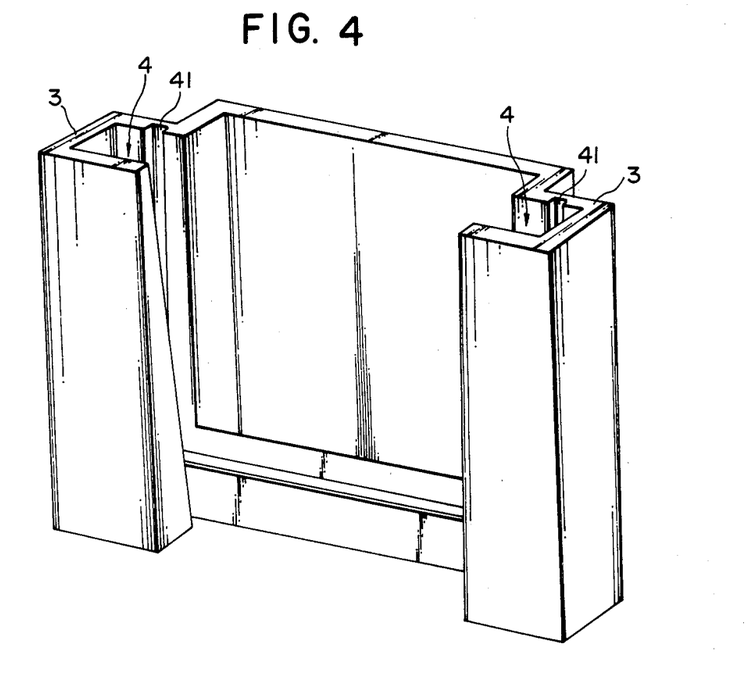
FIG. 4 is a perspective view of an embodiment of the glass support column portions.
Figure 5:
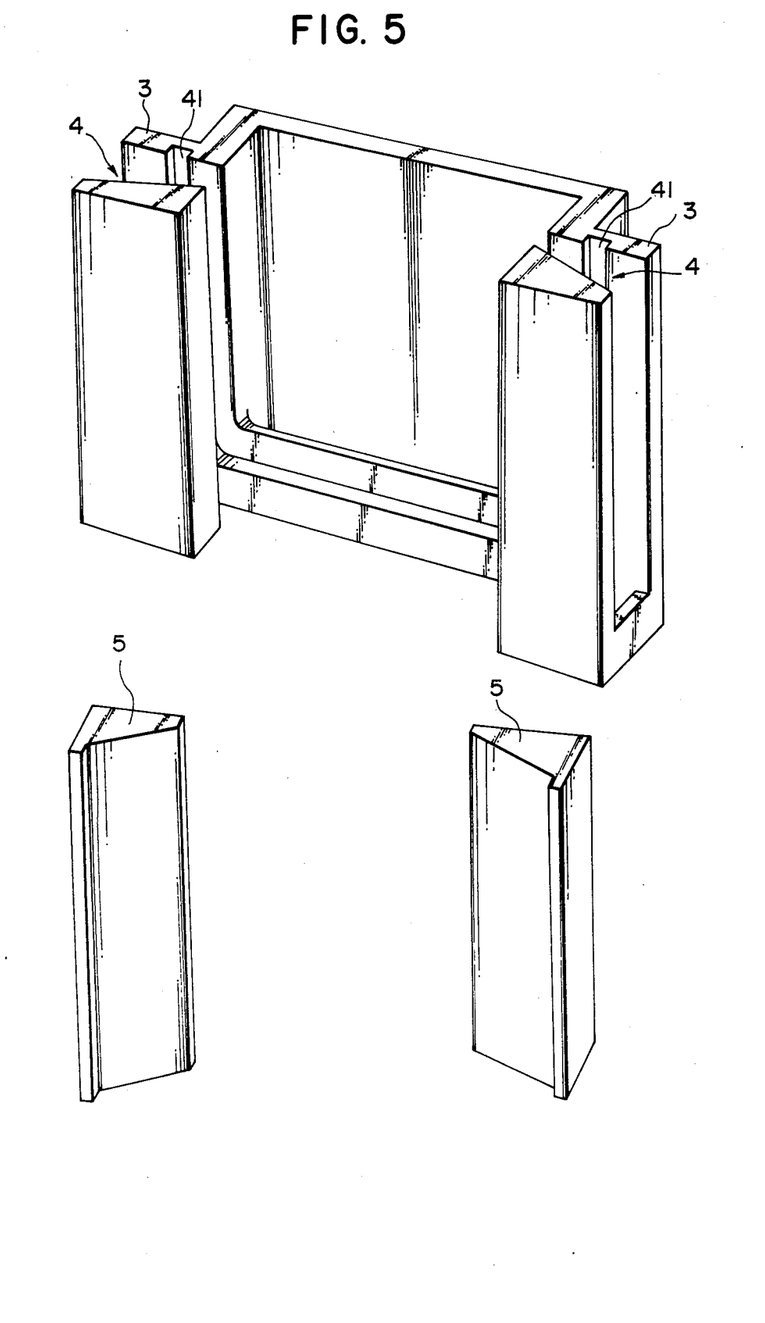
FIG. 5 to 7 are perspective views showing in separated state the glass support column portions and wedge-like fixing bars of modified constructions.
Figure 6:
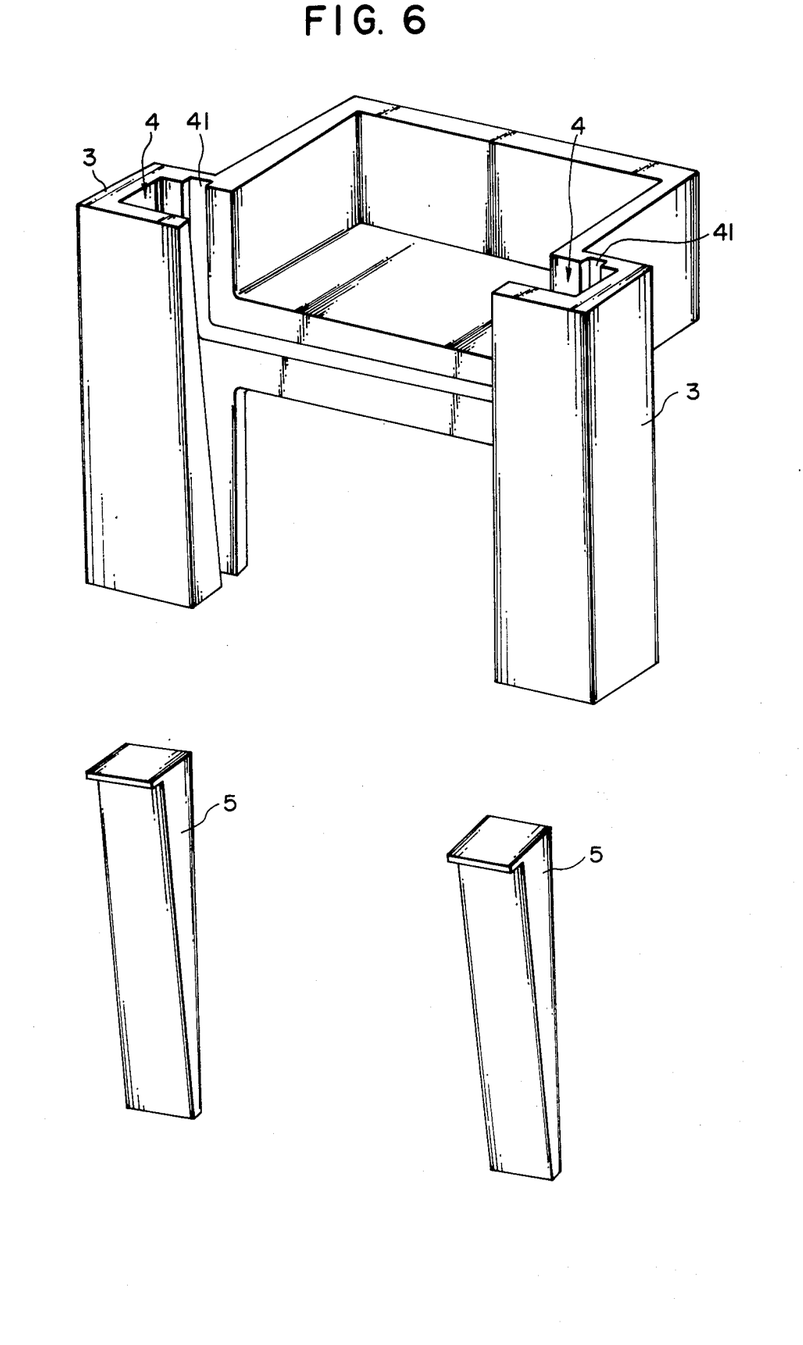
Figure 7:
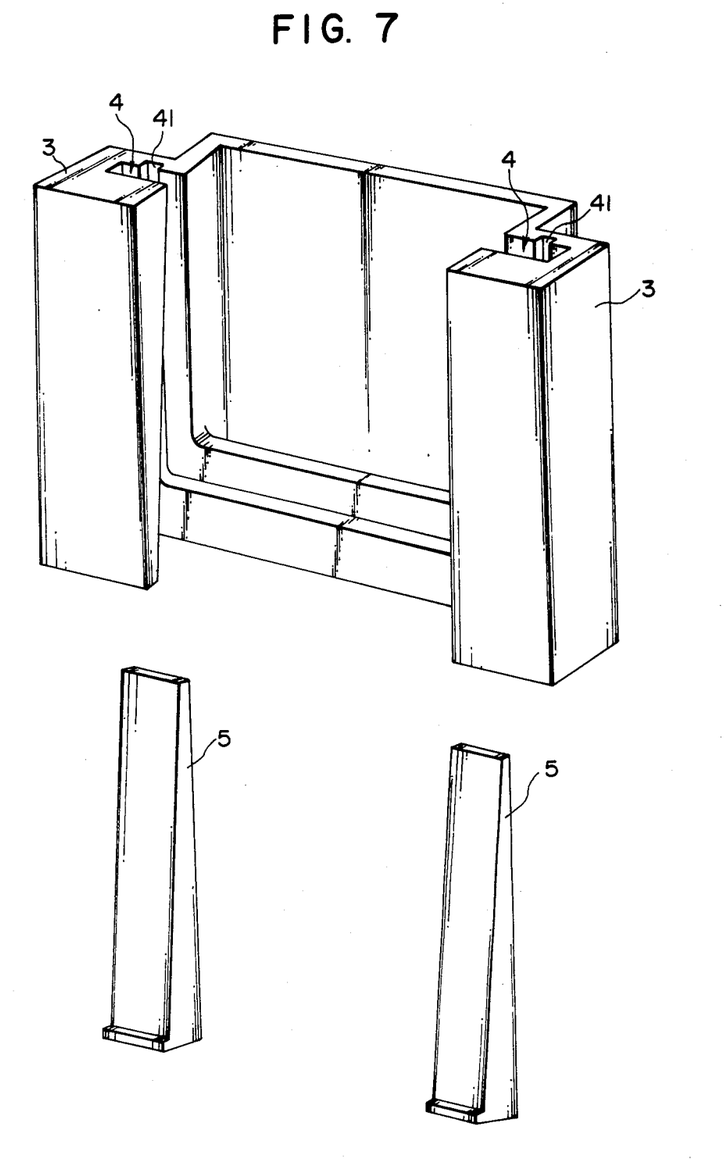

The glass support column portions 3 are each provided with tapered fitting groove 4 for receiving therein the glass sheet couple 1 and wedge-like fixing bars as will be described hereinlater, the fitting groove 4 being formed opposingly and tapered along the entire length of the glass support column portions 3. The tapered fitting groove 4 is broadened toward an opening through which the wedge-like fixing bar is inserted, for instance, toward the upper side (FIGS. 4 and 6), toward the lower side (FIG. 7) or toward the lateral side (FIG. 5).

Designated at 5 are the wedge-like fixing bar which have an outer shape corresponding to the inner wall shape of the glass fitting groove 4, and inserted into the latter after fitting the opposite sides of the gel holding glass sheet couple 1 in the groove 4, thereby detachably fixing the glass sheet couple 1 in the groove 4. The column portions 3 and wedge like fitting 5 together form means for detachably securing the glass sheet couple to the cooperating chamber forming structure 2.

For fixation of the gel holding glass sheet couple 1, it is desirable to provide packing 6 between the glass sheet couple 1 and the inner wall surface of the fitting groove 4. For this purpose, the glass fitting groove 4 are preferably provided with groove 41 on the inner wall surfaces for receiving the packing 6.

With the apparatus of the invention as described above, the gel holding glass sheet couple is fixedly retained in the glass fitting groove on the glass support columns of the liquid buffer chamber by the wedge-like fixing bars, so that substantially uniform pressure is exerted on the glass sheet couple as a whole.

Accordingly, the electrophoresis apparatus of the invention precludes distortion of the gel which is gripped between the coupled glass sheets, permitting to obtain excellent migration images while preventing fracture of the glass sheets.

Figure 1:
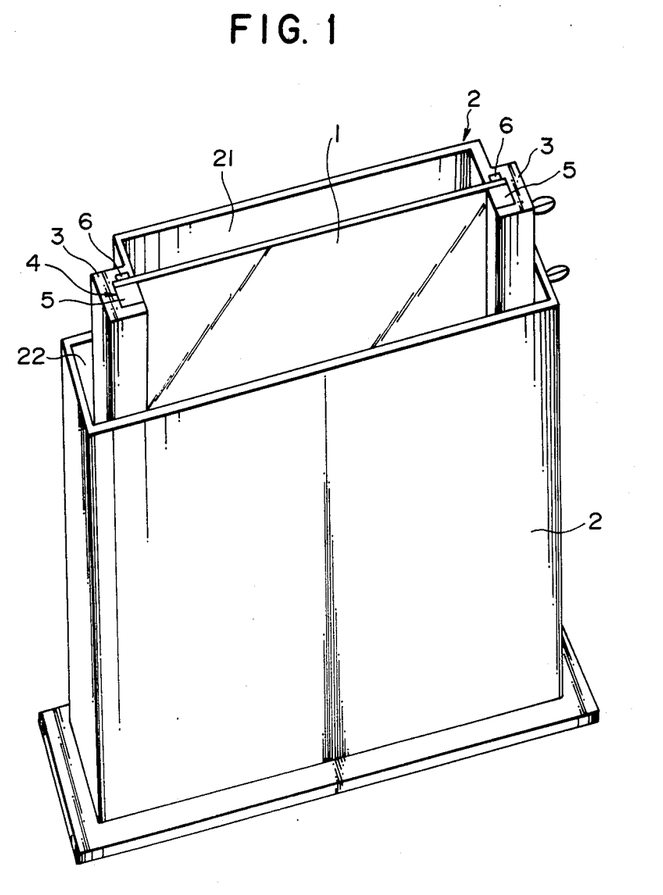
FIG. 1 is a perspective view of an electrophoresis apparatus embodying the present invention, with horizontally juxtaposed buffer liquid chamber.
Figure 2:
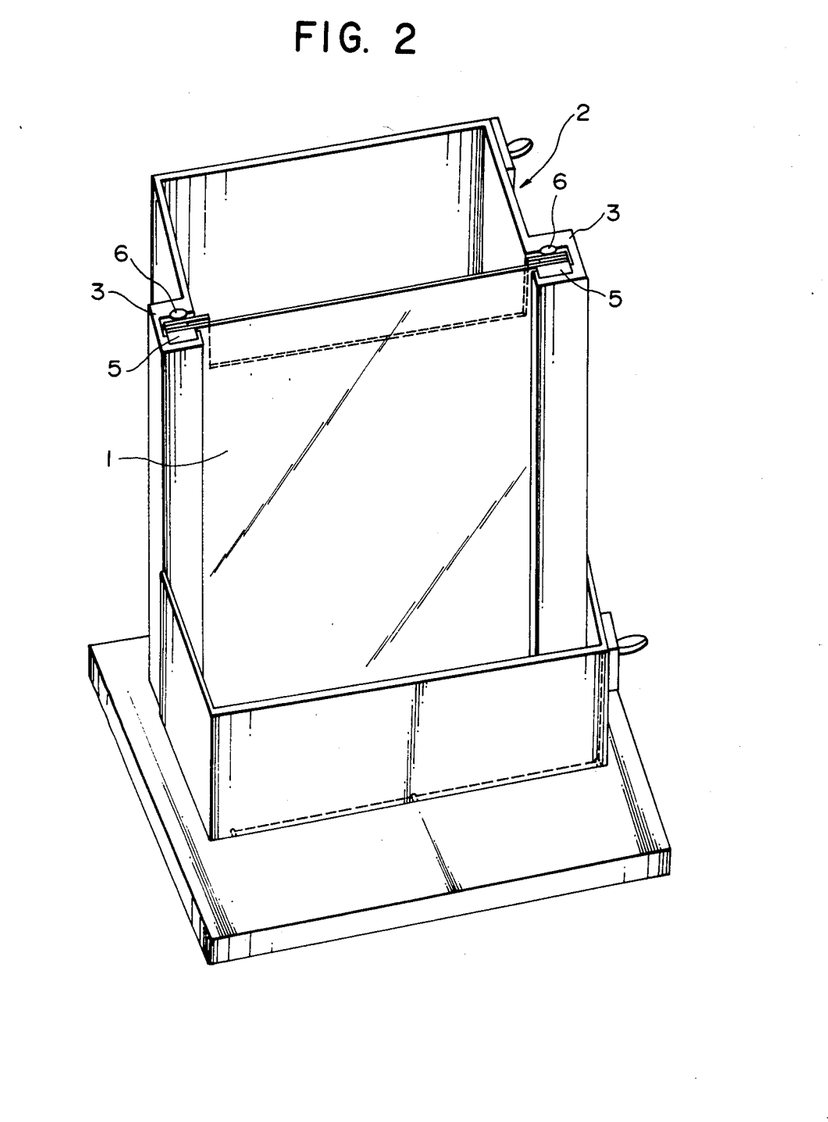
FIG. 2 is a perspective view of an electrophoresis apparatus embodying the present invention, with vertically juxtaposed buffer liquid chambers.
Figure 3:
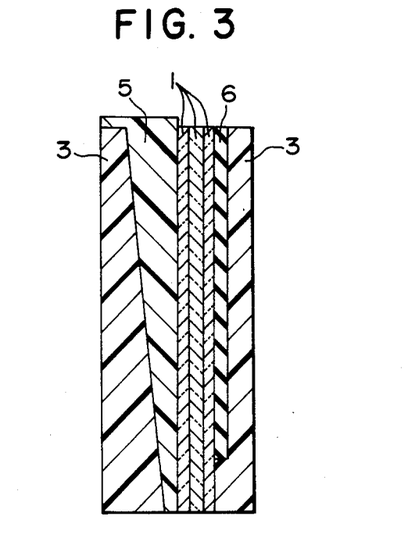
FIG. 3 is an enlarged sectional view employed for the explanation of the manner of holding and fixing a glass sheet couple.

Besides, in case of the electrophoresis apparatus shown in FIG. 1 as an exemplary embodiment of the invention, it is possible to increase the height of the outer buffer liquid chamber 21 and cool the gel holding glass sheet couple from both of the inner and outer buffer liquid chambers 22 and 21, allowing to conduct the electrophoresis with higher voltage and current as compared with conventional counterparts. For example, electrophoresis for a 10×8.6×0.1 cm SDS-polyacrylamide gel using 3 mm thick glass sheets can be conducted with a voltage and a current as high as 500 V and 60 mA, respectively, in a shortened migration time of about 30 minutes without a smile phenomenon of the migration image. When packing is used in combination with the glass sheet couple as shown in FIG. 9, it becomes possible to employ higher voltage (800 V) and current (1000 mA) for the electrophoresis thereby to shorten the migration time and obtain an improved migration image free of the smile phenomenon.

What is claimed is:

1. A vertical slab-type electrophoresis apparatus, comprising:
    a gel holding glass sheet couple;
    chamber forming means for cooperating with said gel holding glass sheet couple to form at least one buffer solution chamber; and
    means for detachably securing said glass sheet couple to said chamber forming means to form said buffer solution chamber, comprising:
    (a) a pair of spaced elongated support columns fixed to said chamber forming means, each of said support columns including means for forming a tapered fitting groove extending along the length of said support column, fitting grooves of each of said support columns being in facing opposition to one another, whereby said glass sheet couple may be fitted into said grooves of said pair of columns,
    (b) a wedge like fitting bar fittable in each said fitting groove to secure said glass sheet couple, when said glass sheet couple is also fitted into said fitting grooves, to said chamber forming means, and
    (c) an additional groove in each said column and running in a direction parallel to the said tapered fitting grooves, said additional groove being capable of receiving a packing situated between the glass sheet couple and the inner wall surface of said fitting groove,
    wherein each said fitting bar has an outer shape corresponding to an inner shape of one of said fitting grooves and a major surface for contacting said glass sheet couple when said fitting bar and glass sheet couple are both fitted in said fitting groove.

2. The vertical slab-type electrophoresis apparatus of claim 1, wherein said columns are elongated the said gel holding glass sheet couple comprises one glass sheet having an indented edge extending between said columns and an other glass sheet provided with a corresponding straight edge extending between said columns.

3. The vertical slab-type electrophoresis apparatus of claim 1, wherein the said gel holding glass sheet couple comprises of a pair of straight-edged glass sheets having different heights or lengths.

4. The vertical slab-type electrophoresis apparatus of claim 1, wherein the said tapered fitting grooves have a maximum width towards an opening through which the wedge-like fixing bars may be inserted.

5. The vertical slab-type electrophoresis apparatus of claim 1, wherein said columns ar elongated and the said tapered fitting grooves each have a maximum width at one end of a corresponding one of said columns.

6. The vertical slab-type electrophoresis apparatus of claim 1, wherein said columns are elongated and the said tapered fitting grooves have a maximum width towards sides of the said apparatus transverse to the direction of elongation of said columns.

7. The apparatus of claim 1 wherein a length of said columns is at least equal to that of said glass sheet couple.

* * * * *

UNITED STATES PATENT AND TRADEMARK OFFICE
CERTIFICATE OF CORRECTION

PATENT NO.    : 4,772,373
DATED         : Sep. 20, 1988
INVENTOR(S)   : Nobuyoshi EBATA et al.

It is certified that error appears in the above-identified patent and that said Letters Patent is hereby corrected as shown below:

On the Title Page, Item [30]:

The Priority Data should be corrected to read as follows:

-- Nov. 29, 1985 [JP]   Japan..................... 60-268645 --

Signed and Sealed this

Twenty-fourth Day of January, 1989

Attest:

DONALD J. QUIGG

*Attesting Officer*          Commissioner of Patents and Trademarks